United States Patent
Arumugam (10) Patent No.: US 10,352,680 B2
(45) Date of Patent: Jul. 16, 2019

(54) THROUGH-THE-WALL MAGNETOQUASISTATIC POSITIONING

(71) Applicant: CALIFORNIA INSTITUTE OF TECHNOLOGY, Pasadena, CA (US)

(72) Inventor: Darmindra D. Arumugam, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 278 days.

(21) Appl. No.: 15/339,663

(22) Filed: Oct. 31, 2016

(65) Prior Publication Data

US 2017/0131080 A1 May 11, 2017

Related U.S. Application Data

(60) Provisional application No. 62/251,304, filed on Nov. 5, 2015.

(51) Int. Cl.
  *G01B 7/004* (2006.01)
  *G01R 29/08* (2006.01)
  *G01N 27/72* (2006.01)

(52) U.S. Cl.
  CPC ......... *G01B 7/004* (2013.01); *G01R 29/0871* (2013.01); *G01N 27/72* (2013.01)

(58) Field of Classification Search
  CPC ........ G01B 7/004; G01N 27/72; G01R 29/08; G01R 29/0871; G01R 29/0892
  See application file for complete search history.

(56) References Cited

U.S. PATENT DOCUMENTS

| 4,314,251 A * | 2/1982 | Raab | G01S 3/14 324/207.24 |
| 6,757,557 B1 | 6/2004 | Bladen et al. | |
| 8,723,509 B2 | 5/2014 | Patterson, III et al. | |
| 9,638,521 B2 | 5/2017 | Arumugam et al. | |
| 2006/0267833 A1* | 11/2006 | Langford | G01S 5/0252 342/174 |
| 2014/0266164 A1* | 9/2014 | Arumugam | G01B 7/004 324/207.15 |

(Continued)

OTHER PUBLICATIONS

Arumugam, D. "Decoupled Range and Orientation Sensing in Long-Range Magnetoquasistatic Positioning", IEEE Antennas and Wireless Propagation Letters, vol. 14, pp. 654-657, (2015).

(Continued)

*Primary Examiner* — Son T Le
*Assistant Examiner* — Dustin R Dickinson
(74) *Attorney, Agent, or Firm* — Steinfl + Bruno, LLP (57) ABSTRACT

Magnetoquasistatic through-the-wall non-line-of-sight coupling between a mobile transmitting device located within a building, or indoor, and a fixed receiving device located outside the building, outdoor, enables positioning of the transmitting device through the wall of the building and in non-line-of-sight environments. Systems based on magnetoquasistatic coupling can separately sense the distance and orientation of the transmitting device accurately even in heavy non-line-sight environments such as steel-reinforced buildings. The approach permits sensing and determination of location and attitude of mobile devices in buildings and can be used to locate rescue workers, first responders, or law enforcement officers inside a building.

20 Claims, 8 Drawing Sheets

(56) References Cited

U.S. PATENT DOCUMENTS

2016/0097656 A1      4/2016    Arumugam et al.

OTHER PUBLICATIONS

Arumugam, D. et al., "Higher Order Loop Corrections for Short Range Magnetoquasistatic Position Tracking", 2011 IEEE International Symposium on Antennas and Propagation (AP-S/URSI), pp. 1755-1757, (2011).

Arumugam, D.D. et al., "Error Reduction in Magnetoquasistatic Positioning Using Orthogonal Emitter Measurements", IEEE Antennas and Wireless Propagation Letters, vol. 11, pp. 1462-1465, (2012).

Arumugam, D.D. et al., "Experimental Demonstration of Complex Image Theory and Application to Position Measurement", IEEE Antennas and Wireless Propagation Letters, vol. 10, pp. 282-285, (2011).

Arumugam, D.D. et al., "Three-Dimensional Position and Orientation Measurements Using Magneto-Quasistatic Fields and Complex Image Theory", IEEE Antennas and Propagation Magazine, vol. 56, No. 1, pp. 160-173, (Feb. 2014).

Arumugam, D.D. "Full-Wave Exact Integral Solutions of a Current Carrying Loop in a General Half-Space" *2013 IEEE Antennas and Propagation Society International Symposium (APSURSI), Institute of Electrical and Electronics Engineers*.2013. pp. 1038-1039.3 pp.

Bannister et al. "Modified Image Theory Quasi-Static Range Subsurface-to-Subsurface and Subsurface-to-Air Propagation Equations" *NUSC Technical Report, Naval Underwater Systems Center*. Oct. 1977. No. 5647. 38 pp.

De Angelis et al. "An Indoor AC Magnetic Positioning System" *IEEE Transactions on Instrumentation and Measurement, Institute of Electrical and Electronics Engineers*. May 2015. vol. 64, No. 5. pp. 1275-1283. 9 pp.

Denis, B. et al., "Impact of NLOS Propagation upon Ranging Precision in UWB Systems", IEEE Conference on Ultra Wideband Systems and Technologies, pp. 379-383, (Nov. 16-19, 2003).

Fang, D.G. et al., "Discrete Image Theory for Horizontal Electric Dipoles in a Mulitlayered Medium", IEEE Proceedings on Microwaves, Antennas and Propagation, 135(5), pp. 297-303, (Oct. 1988).

Jiang, Z. et al., "NLOS GPS Signal Detection using a Dual-Polarisation Antenna", GPS Solutions, vol. 18, pp. 15-26, (2014).

Koutsou, A.D. et al., "Preliminary Localization Results With an RFID Based Indoor Guiding System", Intelligent Signal Processing, IEEE International Symposium, pp. 1-6, (2007).

Kriezis, E.E. et al., "Eddy Current Distribution and Loss in a Semi-Infinite Conducting Space Due to a Vertical Current Loop", ETZ Archive, pp. 201-207, (Jul. 1979).

Notice of Allowance for U.S. Appl. No. 14/876,736 filed Oct. 6, 2015 on behalf of California Institute of Technology. dated Jan. 26, 2017. 9 pages.

Raab, F.H. "Quasi-Static Magnetic-Field Technique for Determining Position and Orientation", IEEE Transactions on Geoscience and Remote Sensing, vol. GE-19, No. 4, pp. 235-243, (Oct. 1981).

Raab, F.R. et al., "Magnetic Position and Orientation Tracking System", IEEE Transactions on Aerospace and Electronic Systems, vol. AES-15, No. 5, pp. 709-718, (Sep. 1979).

Reynolds, M. "Low Frequency Indoor Radiolocation", Ph.D. Dissertation, Media Arts and Sciences, MIT, (2003). 141 pages.

Schweizer, J. et al., "Testing the Performance of Avalanche Transreceivers", Cold Regions Science and Technology, 37, pp. 429-438, (2003).

Wait, J.R. "Image Theory of a Quasistatic Magnetic Dipole Over a Dissipative Half Space" *Electronics Letters, Institute of Electrical and Electronics Engineers*.Jun. 1969. vol. 5, No. 13. pp. 281-282. 3 pages.

\* cited by examiner

THROUGH-THE-WALL MAGNETOQUASISTATIC POSITIONING

CROSS REFERENCE TO RELATED APPLICATIONS

The present application claims priority to U.S. Provisional Patent Application No. 62/251,304, filed on Nov. 5, 2015, and may be related to U.S. patent application Ser. No. 14/876,736, filed on Oct. 6, 2015, the disclosures of which are incorporated herein by reference in their entirety.

STATEMENT OF INTEREST

The invention described herein was made in the performance of work under a NASA contract NNN12AA01C, and is subject to the provisions of Public Law 96-517 (35 USC 202) in which the Contractor has elected to retain title.

TECHNICAL FIELD

The present disclosure relates to location sensing using quasi-stationary magnetic fields. More particularly, it relates to through-the-wall magnetoquasistatic positioning for a mobile device located in a non-line-of-sight indoor building environment, where the mobile device emits a quasi-stationary or quasi-static magnetic field which is sensed outside the building.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

In a first aspect of the disclosure, a method is described, the method comprising: providing at least one transmitter configured to transmit a magnetoquasistatic field, the at least one transmitter comprising at least two coils orthogonal to each other, the at least two coils each having, during operation, an equivalent magnetic moment parallel to a horizontal plane formed by a y axis and an x axis, the y axis being perpendicular to a surface of an external wall of the building, and the x axis being orthogonal to the y axis and parallel to the surface of the external wall; providing at least one receiver configured to detect the magnetoquasistatic field, the at least one receiver being located outside the building; transmitting, through the external wall, the magnetoquasistatic field with the at least one transmitter; measuring, through the wall, the magnetoquasistatic field with the at the at least one receiver; approximating the building as a homogeneous conducting body for penetration of the magnetoquasistatic field; decoupling a range and orientation of the at least one transmitter relative to the at least one receiver; and based on the approximating and decoupling, measuring a first coordinate position, along the y axis, between the at least one transmitter and the external wall, and a second coordinate position, along the x axis, for the at least one transmitter.

DETAILED DESCRIPTION

The present disclosure describes the magnetoquasistatic (MQS) coupling between a mobile transmitting device located within a building (indoor) and a receiving device located outside the building (outdoor). In some embodiments, the receiving device may be in a fixed location. In some embodiments, the magnetoquasistatic coupling is described with the assumption that the building can be approximated as a homogeneous conducting body for penetration of the fields within a few skin-depths into the building, due to the long wavelength MQS field. Due to the low-frequencies used in the technique, the skin-depth can be very large, and therefore a large portion of most buildings can be considered as a homogenous conducting medium. The theory described herein permits decoupled sensing of range and orientation of the mobile device when multi-axis devices are used. The present disclosure also describes devices and methods based on magnetoquasistatic coupling. The theory is described, in an example, in an industrial building and demonstrates ranging with an average error of 0.42 m in a steel-reinforced building, with the expectation of significantly lower errors in residential dwellings such as houses.

A magnetoquasistatic field is a class of electromagnetic field in which a slowly oscillating magnetic field is dominant. In some embodiments, the quasistatic range can be understood considering the distance between a sensor and the object to be detected, r, and the wavelength of the electromagnetic field, $\lambda$. In some embodiments, the quasistatic range is effective when $r \ll \lambda$.

Through-the-wall non-line-of-sight (NLoS) positioning is a useful technology in several fields; in particular, it is critical in homeland security and military applications. Due to the lack of penetrability or multi-path scattering, existing high-frequency propagation-based techniques suffer in NLoS use (for example, see Refs. [1] and [2]). In contrast, magnetoquasistatic (MQS) fields are weakly perturbed by lossy dielectrics and provide accurate positioning in NLoS environments, see for example Refs. [3] and [4].

Existing MQS positioning systems include short range systems (Ref. [5]) and short-to-long range systems (Refs. [3] and [4]). Short-range MQS systems use a low frequency of a few kilohertz to avoid ground effects, as described in Ref. [5]. However, the low frequency and the increased ground effects with range are disadvantages that limit their operation to a few meters. Short to long range systems use a higher frequency of up to a few hundred kilohertz, operating still well within the quasistatic range ($r \ll \lambda$), to enable positioning up to many tens of meters, see Ref [3]. To enable accurate positioning, short to long range systems account for secondary fields due to the ground, or nearby electrically large conductors, as described in Ref. [3].

Homeland security applications such as first responder or fire fighter search and rescue operations, and related military applications, can benefit immensely from accurate through-the-wall NLoS positioning using MQS fields. The goal is to obtain accurate position and orientation of a first responder carrying a mobile MQS device, by sensing the field of the mobile device outside the building, using a fixed receiver device located on a fire truck or similar vehicle. In other embodiments, the receiver may also be a mobile device and may not be housed in a vehicle. Whether a device is mobile or fixed largely depends on its weight, dimensions, and power requirements. Therefore, advances in technology may render fixed devices mobile while conserving a similar function as pertinent to the novel aspects of the technology described in the present disclosure. However, in the present disclosure, a fixed device can also be considered as a device that is in a fixed location and is not moving, while the mobile device inside the building is moving. For example, the vehicle hosting the fixed device may be stationary outside the building, while the mobile device can be carried by a worker moving inside the building.

While MQS fields have been studied for a very limited number of indoor applications (see Refs. [6] and [7]), previous works do not enable the sensing of an indoor mobile device using an outdoor sensor, and do not permit orientation sensing or out-of-plane position sensing. In addition, previous works can also be very limiting due to the reliance on arbitrary power-law fitting (as in Ref. [6]) or operation at short-ranges (e.g., limited to 3 m×3 m) in an indoor line-of-sight (LoS) environment, as in Ref. [7]. The present disclosure describes a MQS technique to enable through-the-wall position and orientation sensing of a mobile indoor device using an outdoor sensor in a multi-path NLoS environment.

Approximated Through-the-Wall Coupling

Figure 1:
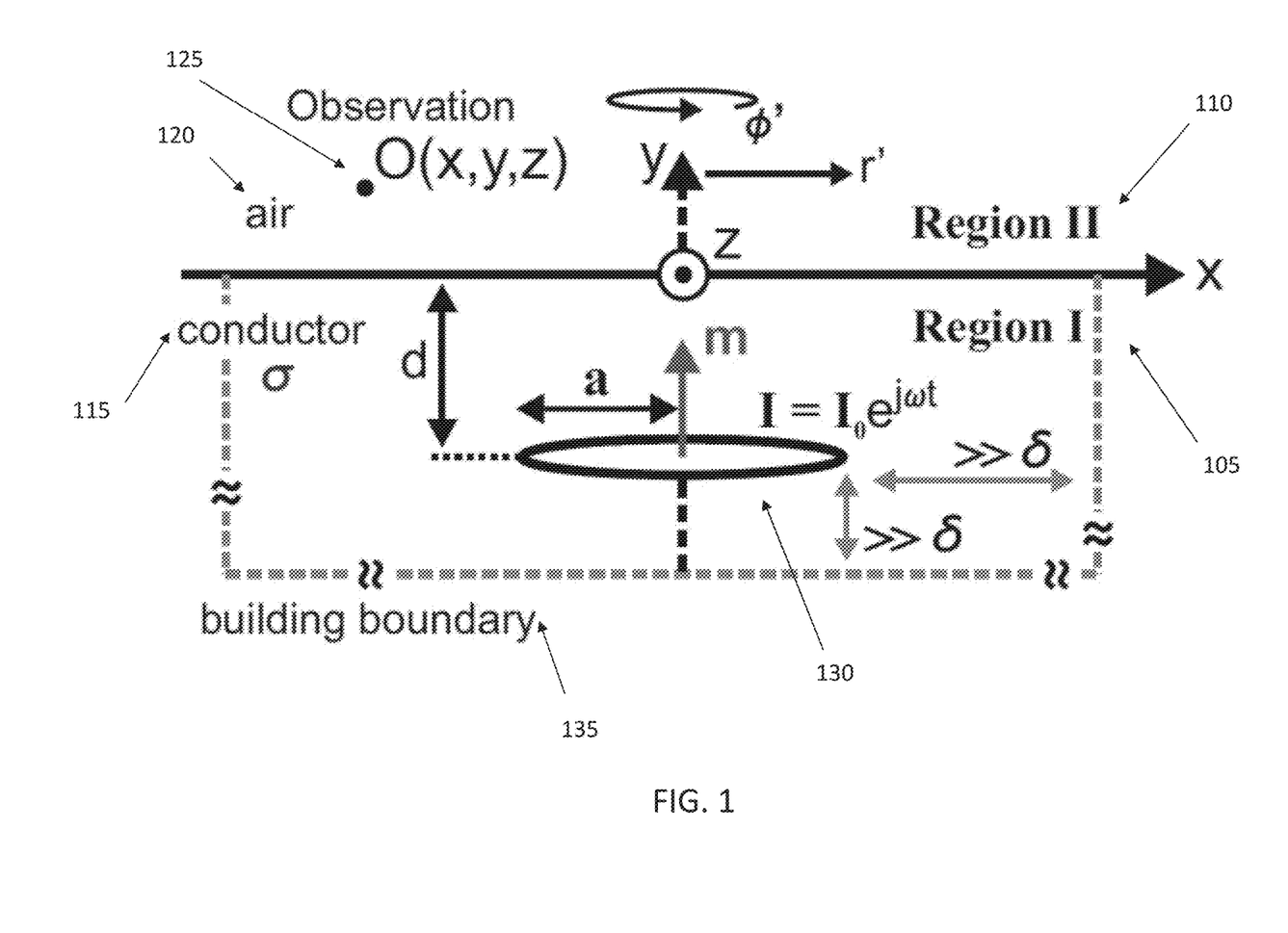
FIG. 1 illustrates an insulated current carrying coil within an electrically-large conductor with a planar air-conductor boundary, for observations in air.

To study the fields of an indoor MQS source, the source being sensed outdoor, it is possible to use an insulated excited coil located within, and parallel to, a semi-infinite conductor and observed outside the conductor, as illustrated in FIG. 1. In FIG. 1, the coil (130) is parallel to the conductor (115). The building boundary (135) is illustrated as a segmented line, with the coil (130) being within the building (135). Two regions are defined, region I (105) and region II (110). The coil is observed in air (120) from a point (125) outside the building boundary. In FIG. 1, the following example is discussed with certain assumptions on the distance of the coil from the building walls. However, in other embodiments, the coil may be positioned at different distances from the walls, different from that of the example of FIG. 1.

Referring to the example of FIG. 1, due to the long-wavelengths of the fields, an effective conductivity can be assumed for the region covering a few skin-depths into the building, considering the coil is positioned at many skin-depths away from the sides and back of the building. The coil distance is indicated as d. With these assumptions, the field of the coil in Region II is $\vec{B} = \nabla \times \vec{A}^{II}$, where $\vec{A}^{II}$ is the magnetic vector potential which has axial symmetry (see for example Ref. [8]):

$$A_{\phi'}^{II}(\rho', y) \approx \frac{\mu_0 I a}{2} \int_0^\infty J_1(\lambda r') J_1(\lambda a) \left[\frac{2\lambda}{\lambda + \alpha}\right] e^{-ad} e^{-\lambda y} d\lambda, \quad (1)$$

where $\alpha = \sqrt{\kappa^2 + \lambda^2}$, $\kappa = 2/(\delta(1-j))$, and $\delta$ is the skin depth of penetration. The eigenfunction transmission coefficient in Eq. (1) can be approximated as in Refs. [9] and [10]:

$$\frac{2\lambda}{\lambda + \alpha} = 1 - \frac{\lambda - \alpha}{\lambda + \alpha} \approx 1 - e^{-\lambda\delta(1-j)} \quad (2)$$

As described in Ref. [10], it is possible to decompose $e^{-ad}$ in Eq. (1), taking the Taylor series expansion of $\alpha = \sqrt{\kappa^2 + \lambda^2}$ with respect to $\lambda = n\kappa$, where n is generally a complex multiplicative constant:

$$\alpha = \frac{\kappa}{\sqrt{1+n^2}} + \frac{n\lambda}{\sqrt{1+n^2}} + O[\lambda - n\kappa]^2 \approx a\kappa + b\lambda, \quad (3)$$

where $a = 1/\sqrt{1+n^2}$ and $b = n/\sqrt{1+n^2}$ are constants to be determined later. The approximation in Eq. (3) permits the decomposition $e^{-ad} \approx e^{-a\kappa d} e^{-b\lambda d}$, as described in Ref. [10], which then gives a new approximate solution for $A_{\phi'}^{II}$ in Eq. (1):

$$A_{\phi'}^{II} \approx e^{-a\kappa d} \left[\frac{\mu_0 I a}{2} \int_0^\infty J_1(\lambda r') J_1(\lambda a) [e^{-\lambda y_s} - e^{-\lambda y_i}] d\lambda\right] \quad (4)$$

where $y_s = y + bd$ and $y_i = y + bd + \delta(1-j)$. From Eq. (4) it is possible to see that, to the observer in Region II (referring to FIG. 1), the source within Region I is at a depth of −y−bd. This depth is shifted from the actual location of −y−d. In addition, a modified complex image exists at a depth of −y−bd−δ(1−j), residing at one complex skin depth further away from the modified source. Both the modified source and its complex image are multiplied by $e^{-a\kappa d}$, which is an exponential attenuation factor due to the medium, but referenced by the original distance of the source from the interface, d. In some embodiments, electrically-small coils are used, which can be described as magnetic dipoles for convenience. The observed magnetic field is then given by:

$$\vec{B}(x,y,z) \approx e^{-a\kappa d} [\vec{B}^d(x,y_s,z) - \vec{B}^d(x,y_i,z)], \quad (5)$$

where the subscripts s and i denote the source and image contributions, respectively, and $\vec{B}^d$ is the vector magnetic field of a quasistatic magnetic dipole given by (as in Ref. [4]):

$$\vec{B}^d(x,y,z) = \frac{\mu_0}{4\pi}\left[\frac{3(\vec{m}\cdot\hat{r})\hat{r} - \vec{m}}{r^3}\right] \quad (6)$$

where $\vec{m}$ is the magnetic moment and $\vec{r}=r\hat{r}$ is the vector centered at the coil's origin. Both source and image fields are attenuated by $e^{-\alpha\kappa d}$, but the image is positioned further and it is thus weaker. It is possible to study the ratio of the y-component field of the image to source on the y-axis, at y=0, and for b≈1 for simplicity:

$$\left.\frac{d^3}{(d+\delta(1-j))^3}\right|_{d=v\delta(1-j)} \to \frac{v^3}{(1+v)^3}, \quad (7)$$

where $d=v\delta(1-j)$ was used. For $1\leq v\leq 3$, Eq. (7) produces $0.1\leq v^3/(1+v^3)\leq 0.4$, which gives an image with signal power between 8 to 18 dB weaker than the source. Therefore, within a few skin-depths into the conductor, a reasonable approximation is to neglect the image field. Although in most building environments it is not necessary to taken into consideration the image fields, due to the large skin depths at low frequencies, in certain applications, such as longer range positioning, the image fields can be taken into account. The voltage measured at a small receive coil in Region II due to a source in Region I is then given by $V=-j\omega[\vec{B}\cdot\hat{n}]a'$:

$$V \approx -j\frac{\omega\mu_0 a'}{4\pi}e^{-\alpha\kappa d}\left[\frac{3(\hat{m}\cdot\hat{r})(\hat{n}\cdot\hat{r}) - \hat{m}\cdot\hat{n}}{r^3}\right], \quad (8)$$

where a' and $\hat{r}$ are the receive coil's surface area and the normal unit vector, respectively, $\vec{r}=x\hat{x}+y_s\hat{y}+z\hat{z}$, and the magnetic moment is assumed to be unity, i.e., $|\vec{m}|=1$ Am$^2$.

Transmitter-Centric Coupled Equations

Figure 2:
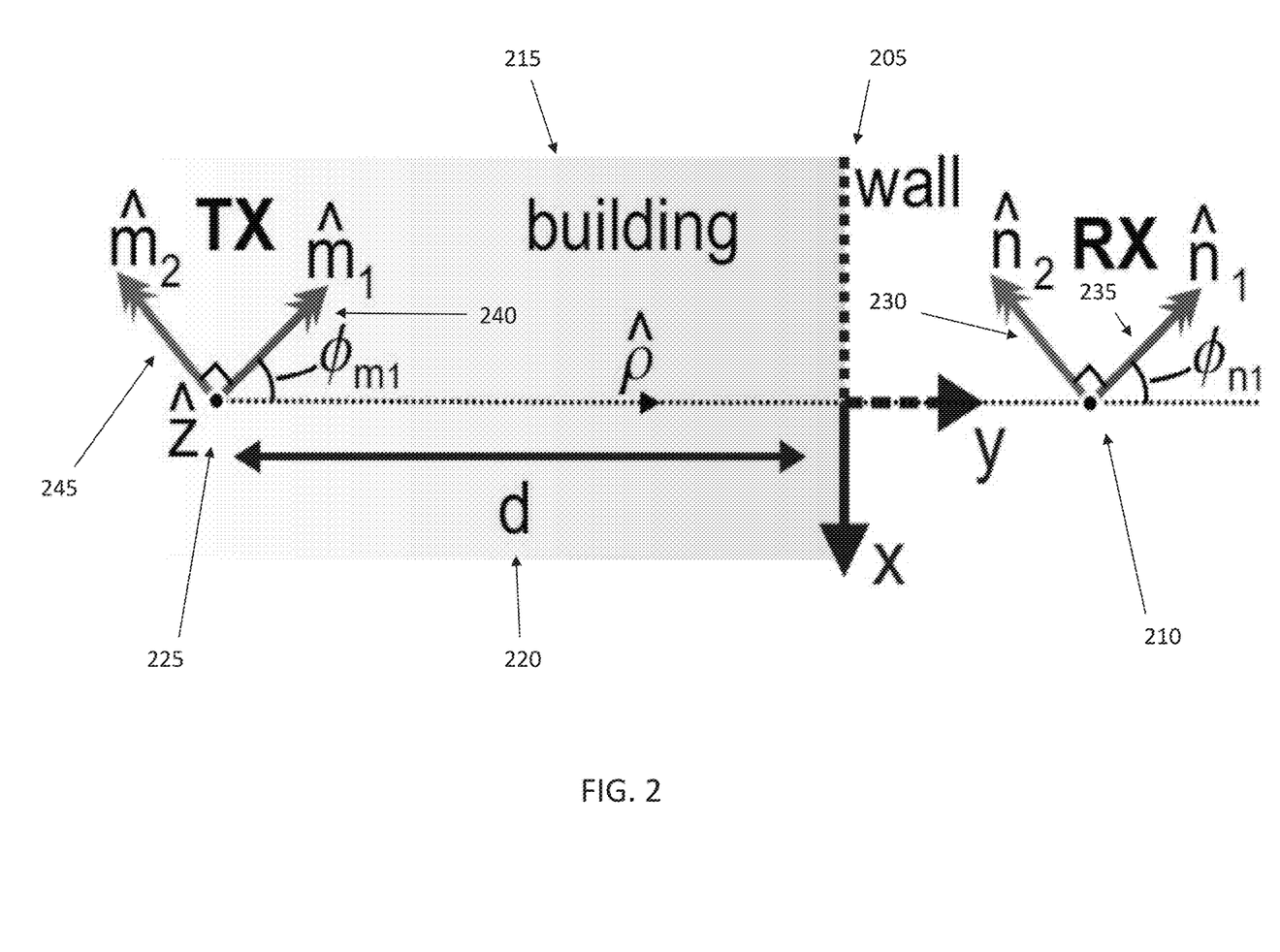
FIG. 2 illustrates a two-axis orthogonal transmitter and receiver configuration for sensing on the two-dimensional plane and through-the-wall, to permit a simplified proof-of-concept experiment and to validate the theory.

The voltage expression in Eq. (8) couples range and orientation of the source and cannot be directly inverted. To permit decoupling, it is possible to use multi-axis orthogonal transmit and receive coils, as in Ref [3]. To simplify the problem for a proof-of-concept examination, it is possible to focus on the two-dimensional (2D) problem on the xy-plane as in FIG. 1, which only requires two orthogonal coils with moments located parallel to the xy-plane, as shown in FIG. 2. In some embodiments, as illustrated in FIG. 2, the xy-plane is horizontal or parallel to ground level.

FIG. 2 illustrates two receive coils (235) and (230), as well as two transmit coils (245) and (240). The voltage measured at the receiver for this 2D case is given by:

$$V \approx c \times e^{-\alpha\kappa d}\left[\frac{3(\hat{m}\cdot\hat{\rho})(\hat{n}\cdot\hat{\rho}) - \hat{m}\cdot\hat{n}}{\rho^3}\right] \quad (9)$$

where $c=-j\omega\mu_0 a'/(4\pi)$ and $\vec{\rho}=x\hat{x}+y_s\hat{y}$. The 2×2 coupling between the transmitter and receiver is described by the transmit-centric equations since it is the range and orientation of the transmitter which are of interest. These are given by:

$$F_{m1} = V_{(m1\to n1)}^2 + V_{(m1\to n2)}^2$$

$$F_{m2} = V_{(m2\to n1)}^2 + V_{(m2\to n2)}^2, \quad (10)$$

where $F_{m1}$ and $F_{m2}$ are the transmit-centric equations for transmitter 1 and 2, respectively. $F_{m1}$ and $F_{m2}$ denote the total power measured due to the transmitter 1 at both receivers, and transmitter 2 at both receivers, see Ref. [3]. As illustrated in FIG. 2, the mathematical treatment below considers a receiver (210) located outside a wall (205), with a transmitter (225) within a building (215), the transmitter being located at a distance d (220) from the wall (205). The transmitter and the receiver, in some embodiments, each comprise two coils orthogonal to each other. In other embodiments, a different number of coils may be used. For example, three coils may be used in a receiver or transmitter, the three coils being orthogonal to each other to enable a complete 3D position and orientation sensing.

As illustrated in FIG. 2, the following quantities can be defined:

$$\hat{m}_1 \cdot \hat{\rho} = \cos\phi_{m1} \quad (11)$$

$$\hat{n}_1 \cdot \hat{\rho} = \cos\phi_{n1}$$

$$\hat{m}_1 \cdot \hat{n}_1 = \cos(\phi_{m1} - \phi_{n1})$$
$$= \cos\phi_{m1}\cos\phi_{n1} + \sin\phi_{m1}\sin\phi_{n1}.$$

Based on the above definition, it is possible to find the voltage due to transmitter $\hat{m}_1$ at receiver $\hat{n}_1$ from Eq. (9), which after simplification gives:

$$V_{(m1\to n1)} \approx c[2\cos\phi_{m1}\cos\phi_{n1} - \sin\phi_{m1}\sin\phi_{n1})] \times \left[\frac{e^{-\alpha\kappa d}}{\rho^3}\right] \quad (12)$$

It is then possible to find the voltage due to transmitter $\hat{m}_1$ at receiver $\hat{n}_2$:

$$V_{(m1\to n2)} \approx c[2\cos\phi_{m1}\cos\phi_{n2} - \sin\phi_{m1}\sin\phi_{n2})] \times \left[\frac{e^{-\alpha\kappa d}}{\rho^3}\right] \quad (13)$$

from which it is possible to find the transmitter-centric equation, $F_{m1}$, by taking the sum of squares $V_{(m1\to n1)}^2 + V_{(m1\to n2)}^2$ using Eq. (10):

$$F_{m1} = \left\{\begin{array}{c}V_{(m1\to n1)}^2 \\ +V_{(m1\to n2)}^2\end{array}\right\} \approx c^2\left[\frac{5+3\cos 2\phi_{m1}}{2}\right] \times \left[\frac{e^{-\alpha\kappa d}}{\rho^3}\right]^2 \quad (14)$$

Similarly, $F_{m2}=V_{(m2\to n1)}^2+V_{(m2\to n2)}^2$ is given by:

$$F_{m2} = \left\{\begin{array}{c}(m2\to n1) \\ +V_{(m2\to n2)}^2\end{array}\right\} \approx c^2\left[\frac{5-3\cos 2\phi_{m1}}{2}\right] \times \left[\frac{e^{-\alpha\kappa d}}{\rho^3}\right]^2 \quad (15)$$

where the substitution $\varphi_{m2}=\varphi_{m1}+\pi/2$ was made to permit writing $F_{m2}$ as a function of $\varphi_{m1}$.

Decoupled Range And Orientation Sensing

In the next steps, it is possible to solve for the decoupled range and orientation of the device. To obtain ranging that is invariant of the orientation, the contributions from both transmit centric equations are summed:

$$F_r = \left\{ \begin{array}{c} F_{m1} \\ +F_{m2} \end{array} \right\} \approx 5c^2 \left[ \frac{e^{-\alpha\kappa d}}{\rho^3} \right]^2 \quad (16)$$

where $\rho = \sqrt{x^2 + (y+bd)^2}$. In practice, $F_r$ can be found by summing the total calibrated power measurements from all field couplings. If the y location of the fixed receiver is known, then Eq. (16) contains two coordinate unknowns for the transmitter, the x location and the d location in the y-direction, the a and b expansion constant unknowns from Eq. (3), and the skin-depth, $\delta$, due to $\kappa=2/(\delta(1-j))$. Because of the device operation within only a few skin-depths from the interface, as required to derive Eq. (8), it is possible to apply an effective bulk value of a and b within that region. The average value of a can be defined as:

$$\bar{a} = \frac{1}{n_2 - n_1} \int_{n_1}^{n_2} \frac{1}{\sqrt{1+n^2}} dn = \frac{\sinh^{-1} n \vert_{n_1}^{n_2}}{n_2 - n_1}, \quad (17)$$

where the average can be found through the integration of Eq. (3) over a range of $n=n_1$ to $n=n_2$. The average b can be found as:

$$\bar{b} = \frac{1}{n_2 - n_1} \int_{n_1}^{n_2} \frac{1}{\sqrt{1+n^2}} dn = \frac{\sqrt{1+n^2}\vert_{n_1}^{n_2}}{n_2 - n_1} \quad (18)$$

As an example, for the region covering about 1 to 4 $\delta_c$, where $\delta_c = \delta(1-j)/2$, or $1 \geq n \geq \frac{1}{4}$, it is possible to find that $\bar{a} \approx 0.84$ and $\bar{b} \approx 0.51$. Replacing $a=\bar{a}$ and $b=\bar{b}$ results in three remaining unknowns in Eq. (16), the x and d location, and $\delta$. If q outdoor receivers are used, a system of equations gives (see Ref. [4]):

$$F_{r,i}^T - F_{r,i}^T = 0, (i=1,2,\ldots,q), \quad (19)$$

where $F_r^T$ denotes the theoretical quantity in Eq. (16) and $F_r^M$ represents the measurements. In some embodiments, a minimum of two diversely located receivers are needed to find the 2D location (the quantities x and d). For $q \geq 2$, the optimal solution can be found through numerical minimization (see Ref. [4]):

$$\Phi = \sum_{i=1}^{q} [F_{r,i}^T - F_{r,i}^M]^2 \quad (20)$$

If the conductivity (or skin-depth) cannot be obtained through calibration measurements with ground truth, then it can be found by minimizing Eq. (20) for $q \geq 3$. As known to the person of ordinary skill in the art, calibration measurements taken at a specific location can be termed as the ground truth for that specific location, as the measurements take into account the physical properties of the materials located at the actual location. For example, a calibration measurement taken with the receivers located outside a specific building and the transmitter(s) located within the building may be termed as the ground truth of that specification location.

To obtain an orientation that is invariant of range, it is possible to take the ratio of the transmit-centric equation, $F_{m2}/F_{m1}$ to find:

$$F_{\phi m} = \frac{F_{m2}}{F_{m1}} = \frac{5 - 3\cos 2\phi_{m1}}{5 + 3\cos 2\phi_{m1}} \quad (21)$$

where both the range dependence and attenuation in Eq. (14) and Eq. (15) are removed. Solving Eq. (21) for $\Phi_{m1}$ gives:

$$\phi_{m1} = \frac{1}{2} \cos^{-1}\left[\frac{5 - 5 \times F_{\phi m}}{3 \times F_{\phi m} + 3}\right] \quad (22)$$

Description of Experiments

To validate the theory and demonstrate ranging, a two-axis orthogonal transmitter and receiver system was developed. The following description illustrates an exemplary embodiment of such a system, and it is not intended to limit the present disclosure to the described example. Different systems may be realized, according to the present disclosure.

In this example, two direct digital synthesizer (DDS) sources are used on the transmitter. Each DDS outputs a tone which is amplified and fed to a resonant coil. In this example, a tone of 67.5 kHz and a tone of 76.5 kHz are used. The tones are sensed at the receiver coils and inverted for range. Additional details on the specific exemplary system can be found in Ref. [3]. The low frequencies are chosen to permit large skin depths on the scale of a many meters, so that the theory is valid over large portions of most buildings (a few skin depths into the building). The highest frequency can be selected to account for the range of validity of the theory as mentioned previously. The reason for selecting the highest valid frequency is to avoid unnecessary loss in signal-to-noise due to very low frequency operation as indicated by Faraday's law, as understood by the person of ordinary skill in the art. In most residential and industrial buildings, this translates to frequencies usually between 5-300 kHz.

In this example, the receiver and transmitter are located at the same height so that the coupling is described by Eq. (9). The mobile transmitter is located inside an industrial steel-reinforced building. The receiver is located on the y-axis of the building as referenced in FIG. 3, panel (a), at y=+2 m, outside the building, with the indoor-outdoor interface of the building being at y=0 m. The coupling is sensed and inverted for the transmitter locations on the y-axis (see FIG. 3, panel (a)) and x-axis (see FIG. 3, panel (b)) of the building.

Figure 3:
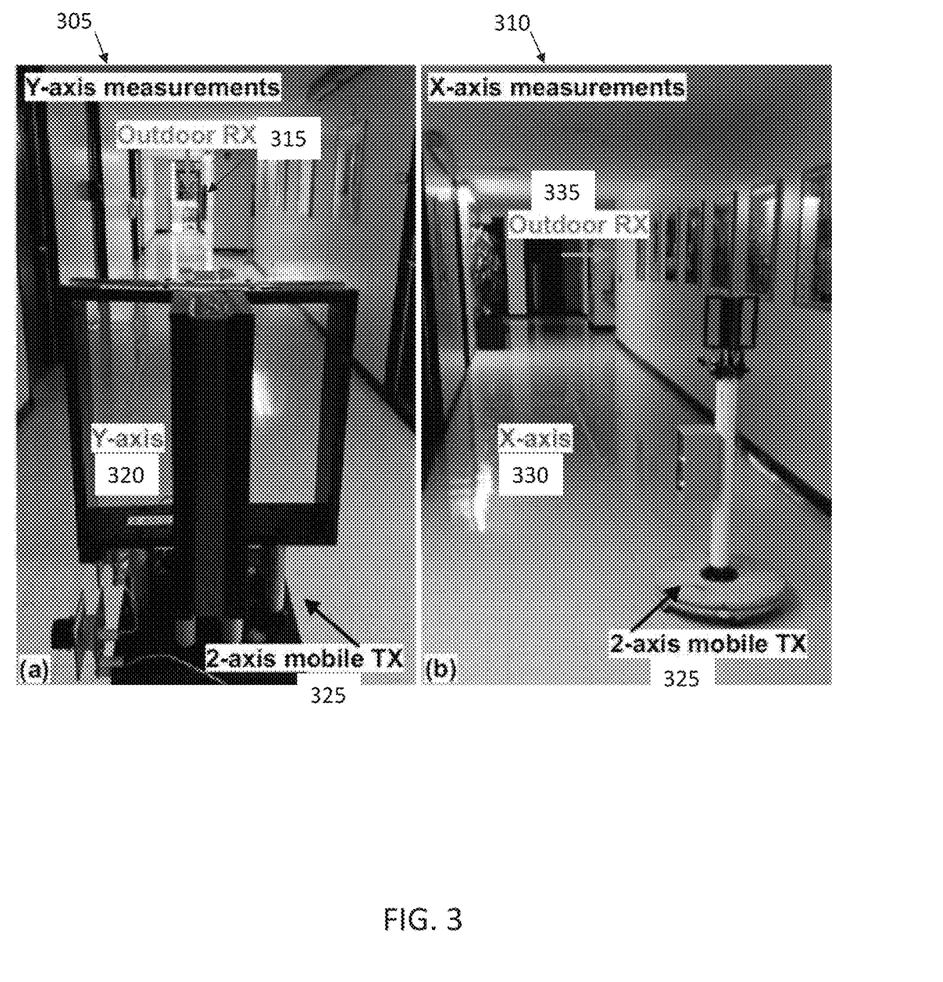
FIG. 3 illustrates an experimental setup using a two-axis mobile MQS transmitter device located within a building, sensed by an external outdoor two-axis receiver system. The transmitter is located on either the y-axis or x-axis of the building, as an example to permit a proof-of-concept experiment.

As illustrated in FIG. 3, a 2-axis mobile transmitter (325) forms part of the system, in this example, together with an outdoor receiver (315). The y axis measurement (305) is along arrow (320), while the x axis measurement (310) is along arrow (330). The same 2-axis mobile transmitter (325) is illustrated in FIG. 3 panel (b) from a different point of view, with the relative location of the outdoor receiver (315) indicated by the arrow (315).

Figure 4:
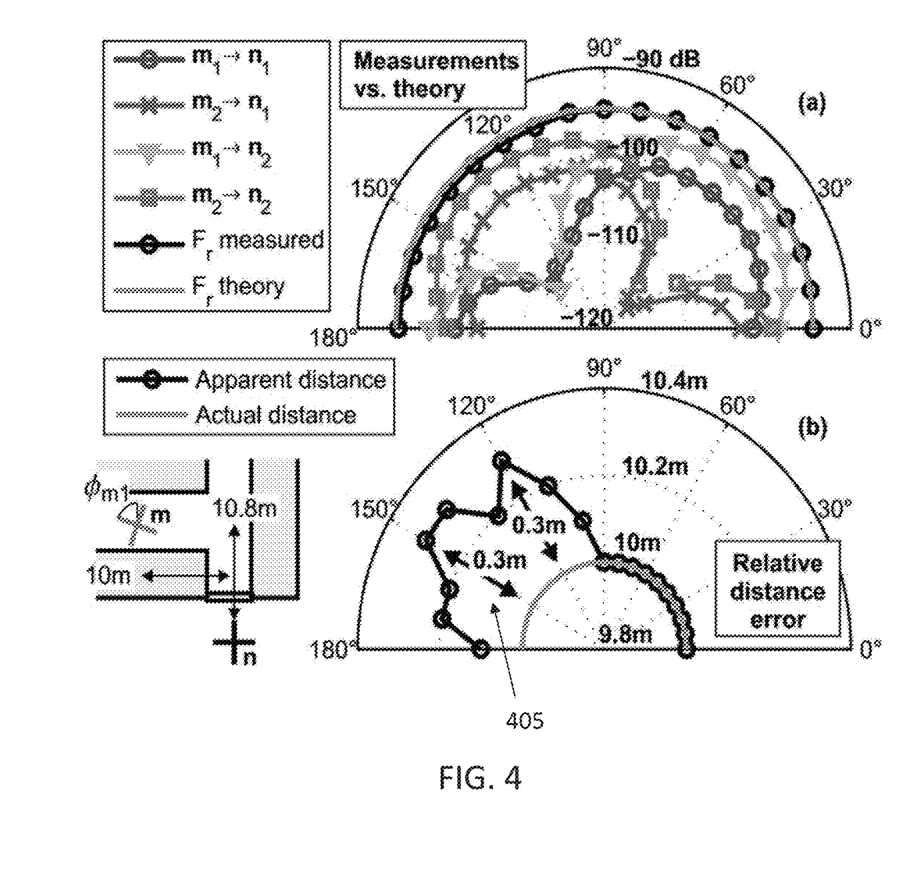
FIG. 4 illustrates the field couplings and orientation-invariant ranging function compared with theory in panel (a). The relative distance error is shown in panel (b).
Figure 5:
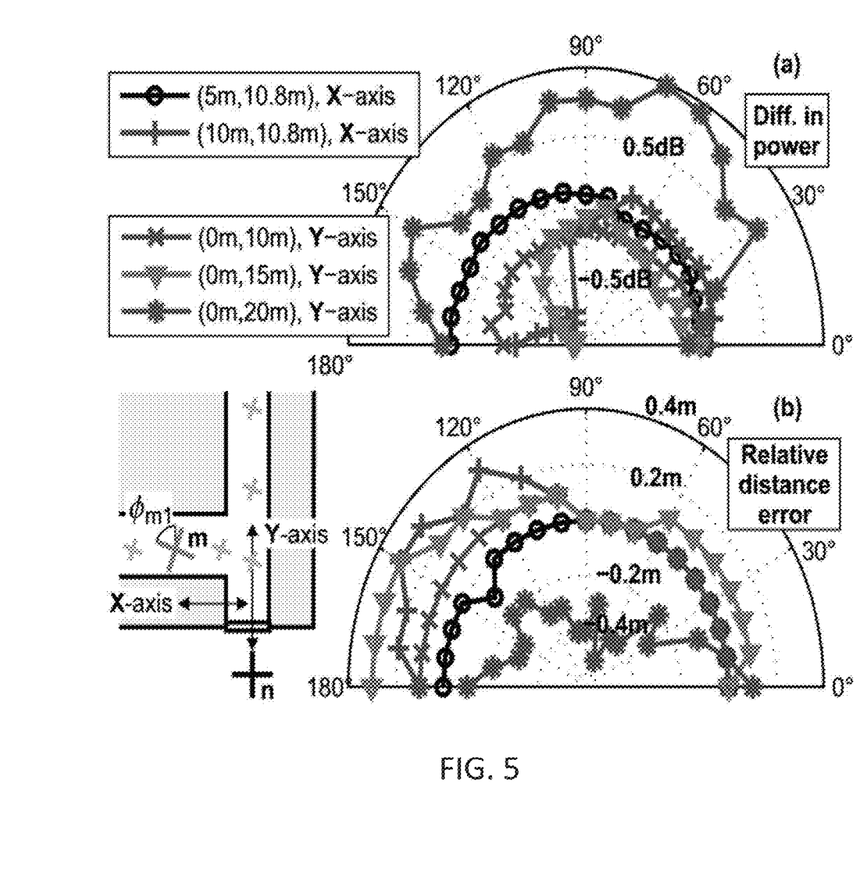
FIG. 5 illustrates the difference in power of the orientation-invariant ranging function at a few locations on the x-axis and y-axis in panel (a). Their respective relative distance error is shown in panel (b).

In the exemplary embodiment, it was first verified that the measurements of the range function, $F_r$, are invariant of the orientation. This can be accomplished by collecting the 2×2 coupling measured at the receiver for various transmitter orientations, $\varphi_{m1}$, as shown in FIG. 4, panel (a) for a transmitter located at $(x,|y+d|)=(10,10.8)$ meters inside the building. To study the distance error due to the orientation only, it is possible to calibrate the measured $F_r$ at $\varphi_{m1}=0°$, and numerically invert the model based on Eq. (16) by fixing $|y+d|=10.8$ m, or $y=2$ m and $d=8.8$ m, and using the approach in Eq. [3] to invert for the x-distance. The resulting inverted distance is compared to the actual distance in FIG. 4 panel (b), showing a maximum error of about 0.3 m (405), where a=0.84 and b=0.51 is used, and $\sigma=0.2$ S/m is found for the effective bulk conductivity through optimization using the approach in Ref. [4]. The value of $\sigma=0.2$ S/m translates to a skin-depth of $\delta \approx 4.3$ m for the frequencies used in this example, so that the region of 1-4 $\delta$ gives a range of about 4.3-17.2 m inside the building. Measurements to study orientation invariance can be repeated at a few locations on the x-axis and the y-axis of the building. The results are shown in FIG. 5 panel (a) for the difference in power between the expected and measured $F_r$, and in FIG. 5 panel (b) for the inverted distance error. The average induced error when measuring the distance, due to orientation variations, is 0.11 m, in this example.

Figure 6:
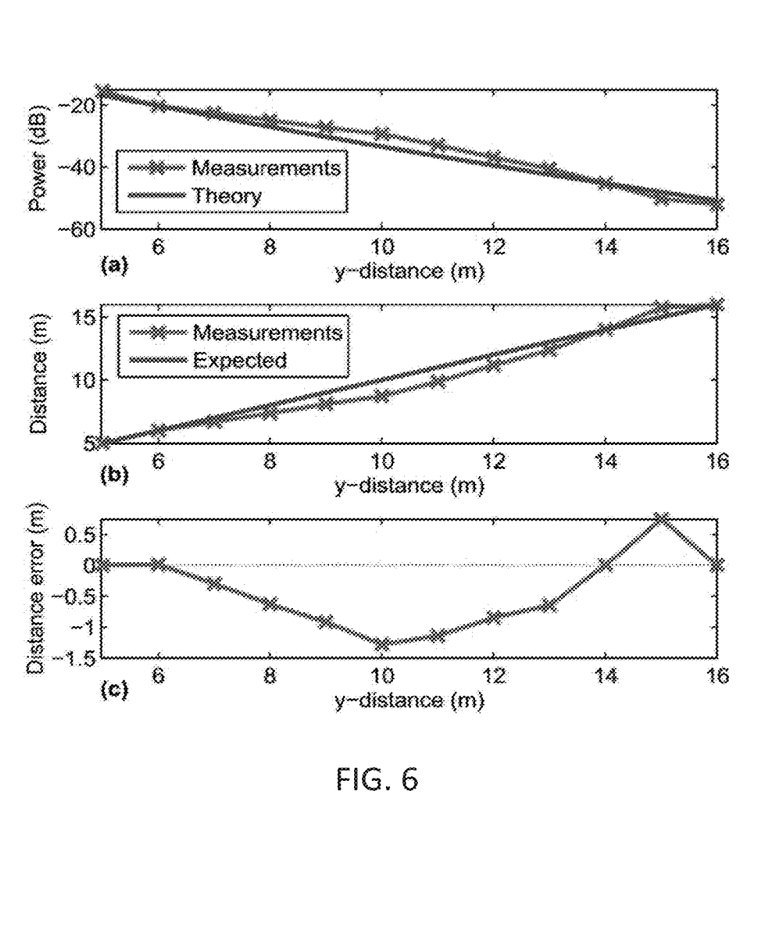
FIG. 6 illustrates the measured orientation-invariant range function compared to theory for measurements on the y-axis of the building in panel (a). The inverted distance is compared to the expected distance in panel (b), and the resulting distance error is shown in panel (c).

To study the ranging accuracy on the y-axis of the building, the transmitter can be moved on the y-axis from d=3-14 m with steps of 1 m each, which corresponds to transmit-receive distances of 5-16 m. The measured $F_r$ is compared to theory in FIG. 6 panel (a) for x=0 m, where the unknown gain in the measurements is calibrated out at a distance of 14 m. The inverted y-distance is compared to the expected distance in FIG. 6 panel (b), and the resulting y-distance error is shown in FIG. 6 panel (c), where the average distance error is 0.54 m.

Figure 7:
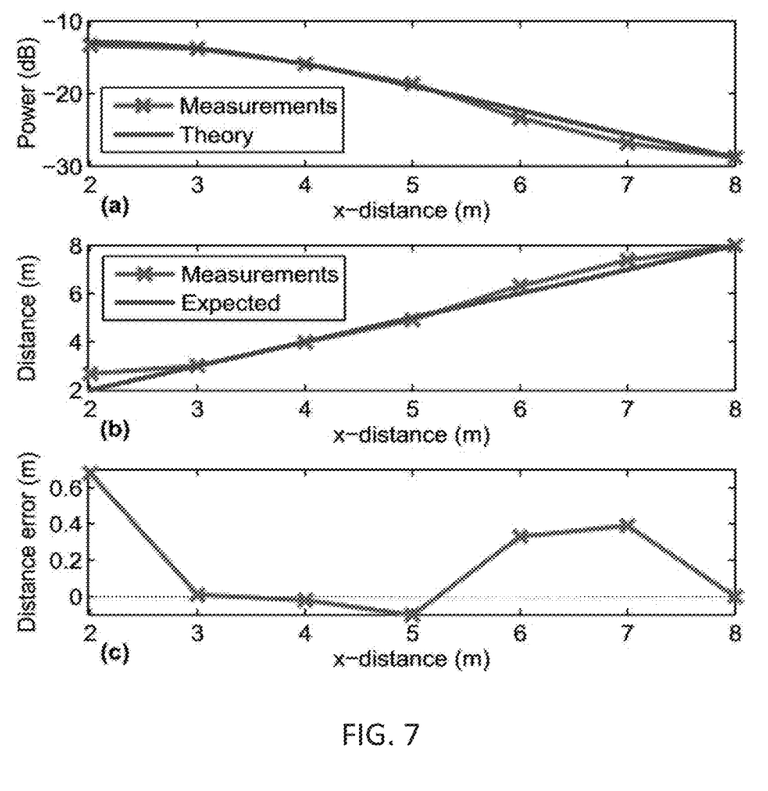
FIG. 7 illustrates the measured orientation-invariant range function compared to theory for measurements on the x-axis of the building in panel (a). The inverted distance is compared to the expected distance in panel (b), and the resulting distance error is shown in panel (c).

To study the ranging accuracy on the x-axis of the building, the transmitter can be moved on the x-axis from x=2-8 m with steps of 1 m each. The measured $F_r$ is compared to theory in FIG. 7 panel (a) for $|y+d|=10.8$ m, where the unknown gain in the measurements is calibrated out at a distance of 8 m. The inverted x-distance is compared to the expected distance in FIG. 7 panel (b), and the resulting x-distance error is shown in FIG. 7 panel (c), where the average distance error is 0.22 m.

The combined x-axis and y-axis measurements show that it is possible to effectively sense the distance to the mobile device at any location within the building with an average error for distance sensing of about 0.42 m, in this example. By using a 3-axis transmitter and receiver, the technique and theory can enable 3D positioning with the same magnitude of error in 3D space, where an additional height dimension can be inverted and sensed.

An approximate MQS coupling theory is described in the present disclosure, and validated for coupling between a transmitter inside a building and a receiver outside the building. It is shown that the building can be approximated as a homogenous conducting body within a few skin-depths from the indoor-outdoor interface. Therefore, the present disclosure enables decoupled range and orientation sensing, and demonstrates distance sensing in the x-axis and y-axis of the building with an average error of 0.42 m.

Therefore, in some embodiments, the present disclosure describes how to obtain decoupled range and orientation measurements for a transmitter within a building, the transmitter being located at a few skin-depths from the wall separating the transmitter within the building to one or more receivers located outside the building. In some embodiments, the distance is measured in the axis that is perpendicular to the wall, which can be defined as the y axis. They axis measurement is therefore within a few skin-depths, regardless of the x position of the transmitter relative to the one or more receivers. In other words, the transmitter is within a few skin-depths from the wall, and if multiple receivers are used, these receivers may be located along the wall, at different positions along the x axis parallel to the wall. In some embodiments, the distance between the transmitter and the remaining walls is several skin-depths, as illustrated for example in FIG. 1. In this context, the walls may be the external walls of a building rather than the internal walls of the building.

In some embodiments, a transmitter being within a few skin-depths of the external wall of the building can be equivalent to less than between 10 and 1 skin-depths of the wall. In some embodiments, a distance much smaller than a wavelength of the field is employed, such that the distance may be smaller than between 0.2 and 0.01 or less times the wavelength.

One improvement of the present disclosure compared to U.S. patent application Ser. No. 14/876,736 (cited above) is that the present disclosure describes techniques and methods for positioning using magnetoquasistatic fields through an electrically large non-line-of-sight embedding medium, such as a wall, surface (metal or dielectric or similar), ground, water body, etc., with the sensor located in air to track a device located inside the electrically large medium. Therefore, the present disclosure permits tracking or navigation in the environments above, where an electrically large medium is lossy and the mobile device is located within the medium. In addition, the medium can contain non-line-of-sight environments. The disclosure from U.S. patent application Ser. No. 14/876,736 describes the basic magnetoquasistatic technique for above ground air-air approach with some electrically small non-line-of-sight occlusions or line-of-sight blockage, however it does not cover the cases when the bulk medium is lossy and contains, in addition, non-line-sight environments, such as in the electrically large embedded mediums described above, and the device is located within the medium.

Figure 8:
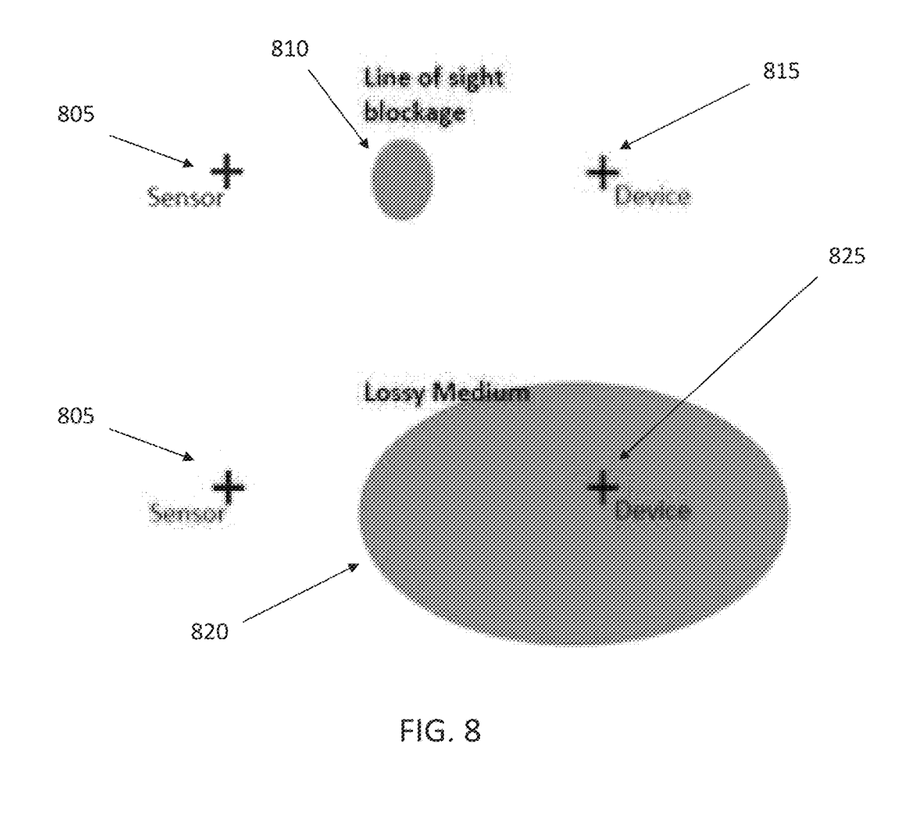
FIG. 8 illustrates positioning in the non-line-of-sight environment, vs. positioning in the embedded non-line-of-sight environment. The embedded non-line-of-sight environment provides a different electromagnetic environment, within which the quasi-static positioning solutions are a variant of the non-line-of-sight quasi-static positioning solutions.

FIG. 8 illustrates an exemplary difference in the operation of the methods described in the present disclosure, and the methods described in U.S. patent application Ser. No. 14/876,736. In FIG. 8, the method of U.S. patent application Ser. No. 14/876,736 allows positioning with a sensor (805) and a second device (815) without obstacles, or with a small lossy obstacle (810). The methods of the present disclosure describe positioning with a sensor (807) and a second device (825), when the device (825) is within a lossy medium (820). In some embodiments, the large lossy medium of FIG. 8 can be understood to be a building having external walls. FIG. 8 does not imply the medium is homogenous, as understood by the person of ordinary skill in the art.

In some embodiments, the determination of the 2D (or 3D) position, and orientation are simultaneously carried out. In some embodiments, one receiver is sufficient to determine orientation of the mobile device. In other embodiments, two or more receivers can be used to determine simultaneous two dimensional position and orientation if the skin depth is known or can be measured. In other embodiments, wherein three or more receivers can be used to determine simultaneous two dimensional position and orientation if the skin depth is not known. In other embodiments, three or more receivers can be used to determine simultaneous three dimensional position and orientation if the skin depth if known or can be measured. In other embodiments, wherein four or more receivers can be used to determine simultaneous three dimensional position and orientation if the skin depth if not known. In some embodiments, the building can be considered as having an internal medium which is electrically lossy, and the environment is a non-line-of-sight environment, as the transmitter and receiver are not in line of sight of each other.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] A. Koutsou, F. Seco, A. Jimenez, J. Roa, J. Ealo, C. Prieto, and J. Guevara, "Preliminary localization results with an rfid based indoor guiding system," in *Intelligent Signal Processing, 2007. WISP 2007. IEEE International Symposium on,* 2007, pp. 1-6.

[2] B. Denis, J. Keignart, and N. Daniele, "Impact of nlos propagation upon ranging precision in uwb systems," in *Ultra Wideband Systems and Technologies, 2003 IEEE Conference on,* 2003, pp. 379-383.

[3] D. Arumugam, "Decoupled range and orientation sensing in long-range magnetoquasistatic positioning," *Antennas and Wireless Propagation Letters. IEEE,* vol. 14, pp. 654-657, 2015.

[4] D. Arumugam, J. Griffin, and D. Stancil, "Experimental demonstration of complex image theory and application to position measurement," *Antennas and Wireless Propagation Letters, IEEE,* vol. 10, pp. 282-285, 2011.

[5] F. Raab, E. Blood, S. T., and J. H., "Magnetic Position and Orientation Tracking System," *IEEE Trans. on Aerospace and Electrical Systems,* vol. AES-15, no. 5, pp. 709-718, 1979.

[6] M. Reynolds, "Low frequency indoor radiolocation," *Ph.D. Dissertation, Media Arts and Sciences,* MIT, 2003.

[7] G. De Angelis, V. Pasku, A. De Angelis, M. Dionigi, M. Mongiardo, A. Moschitta, and P. Carbone, "An indoor ac magnetic positioning system," *Instrumentation and Measurement, IEEE Transactions on,* vol. 64, no. 5, pp. 1275-1283, May 2015.

[8] D. Arumugam, "Full-wave exact integral solutions of a current carrying loop in a general half-space," in *Antennas and Propagation Society International Symposium (APSURSI),* 2013 *IEEE,* July 2013, pp. 1038-1039.

[9] J. Wait, "Image theory of a quasistatic magnetic dipole over a dissipative half-space," in *Electronics Letters,* vol. 5, no. 13, June 1969, pp. 281-282.

[10] P. R. Bannister and R. L. Dube, "Modified image theory quasi-static range subsurface-to-subsurface and subsurface-to-air propagation equations," *NASA STI/Recon Technical Report N,* vol. 78, p. 15372, October 1977.

What is claimed is:

1. A method comprising:
providing at least one transmitter configured to transmit a magnetoquasistatic field, the at least one transmitter comprising at least two coils orthogonal to each other, the at least two coils each having, during operation, an equivalent magnetic moment parallel to a horizontal plane formed by a y axis and an x axis, the y axis being perpendicular to a surface of an external wall of a building, and the x axis being orthogonal to the y axis and parallel to the surface of the external wall;
providing at least one receiver configured to detect the magnetoquasistatic field,
the at least one receiver being located outside the building;
transmitting, through the external wall, the magnetoquasistatic field with the at least one transmitter;
measuring, through the wall, the magnetoquasistatic field with the at least one receiver;
approximating the building as a homogeneous conducting body for penetration of the magnetoquasistatic field;
decoupling a range and orientation of the at least one transmitter relative to the at least one receiver; and
based on the approximating and decoupling, measuring a first coordinate position, along the y axis, between the at least one transmitter and the external wall, and a second coordinate position, along the x axis, for the at least one transmitter.

2. The method of claim 1, wherein the first coordinate position is shorter than one wavelength of the magnetoquasistatic field, and shorter than ten skin-depths.

3. The method of claim 2, wherein the at least one receiver comprises at least two receivers located at different positions along the external wall.

4. The method of claim 3, further comprising:
taking a calibration measurement with ground truth at the building; and
determining the skin-depth based on the calibration measurement.

5. The method of claim 2, wherein the at least one receiver comprises at least three receivers located at different positions along the external wall.

6. The method of claim 1, wherein the at least one receiver comprises at least two receivers, and further comprising simultaneously determining two dimensional position and orientation of the at least one transmitter.

7. The method of claim 6, wherein simultaneously determining two dimensional position and orientation is based on a known skin-depth.

8. The method of claim 6, further comprising measuring a skin-depth, and wherein simultaneously determining two dimensional position and orientation is based on the measured skin-depth.

9. The method of claim 6, wherein the at least two receivers comprise at least three receivers.

10. The method of claim 7, wherein the at least two receivers comprise at least three receivers and further comprising simultaneously determining three dimensional position and orientation of the at least one transmitter.

11. The method of claim 10, wherein simultaneously determining three dimensional position and orientation is based on a known skin-depth.

12. The method of claim 10, further comprising measuring a skin-depth, and wherein simultaneously determining three dimensional position and orientation is based on the measured skin-depth.

13. The method of claim 10, wherein the at least three receivers comprise at least four receivers.

14. The method of claim 4, wherein measuring the magnetoquasistatic field comprises measuring the magnetoquasistatic field on each coil of the at least one receiver transmitted from each coil of the at least on transmitter.

15. The method of claim 14, wherein measuring the magnetoquasistatic field on each coil comprises measuring a voltage on each coil.

16. The method of claim 15, further comprising, based on the approximating and decoupling, measuring the orientation of the at least one transmitter.

17. The method of claim 15, wherein the at least one receiver is at a fixed location relative to the external wall.

18. The method of claim 1, wherein the external wall is electrically lossy.

19. The method of claim 18, wherein an internal medium of the building is electrically lossy.

20. The method of claim 18, wherein the at least one receiver is not in line of sight of the at least one transmitter.

* * * * *